United States Patent [19]

Kaiser et al.

[11] Patent Number: 5,955,408
[45] Date of Patent: Sep. 21, 1999

[54] TRICLOSAN SKIN WASH WITH ENHANCED EFFICACY

[75] Inventors: Nancy E. Kaiser, Pontoon Beach, Ill.; Denise K. Pretzer, Chesterfield, Mo.

[73] Assignee: STERIS Inc., Temecula, Calif.

[21] Appl. No.: 08/890,521

[22] Filed: Jul. 9, 1997

Related U.S. Application Data

[60] Provisional application No. 60/021,453, Jul. 10, 1996.

[51] Int. Cl.$^6$ ................ C11D 1/12; C11D 3/44; C11D 3/48
[52] U.S. Cl. .............. 510/131; 510/119; 510/123; 510/125; 510/130; 510/235; 510/237; 510/342; 510/382; 510/386; 510/405; 510/407; 510/414; 510/432; 510/434; 510/471; 510/477; 510/480
[58] Field of Search ................. 510/119, 123, 510/125, 130, 131, 235, 237, 342, 382, 386, 405, 407, 414, 432, 434, 471, 477, 480

[56] References Cited

U.S. PATENT DOCUMENTS

| | | | |
|---|---|---|---|
| 4,975,218 | 12/1990 | Rosser | 252/117 |
| 5,006,529 | 4/1991 | Resch | 514/721 |
| 5,057,311 | 10/1991 | Kamegai et al. | 424/70 |
| 5,364,031 | 11/1994 | Taniguchi et al. | 239/330 |
| 5,415,810 | 5/1995 | Lee et al. | 252/545 |
| 5,417,875 | 5/1995 | Nozaki | 252/106 |
| 5,635,469 | 6/1997 | Fowler et al. | 510/406 |
| 5,681,802 | 10/1997 | Fujiwara et al. | 510/130 |
| 5,716,626 | 2/1998 | Sakurai et al. | 424/401 |

FOREIGN PATENT DOCUMENTS

| | | |
|---|---|---|
| 2202698 | 10/1973 | France . |
| 3723990 A1 | 7/1987 | Germany . |
| 1408885 | 10/1975 | United Kingdom . |
| WO 96/06153 | of 0000 | WIPO . |
| WO 93/07250 | 4/1993 | WIPO . |
| WO 95/09605 | 4/1995 | WIPO . |
| WO 95/24179 | 9/1995 | WIPO . |
| WO 95/32705 | 12/1995 | WIPO . |
| WO 96/06152 | 2/1996 | WIPO . |

*Primary Examiner*—Yogendra Gupta
*Assistant Examiner*—Charles Boyer
*Attorney, Agent, or Firm*—Fay, Sharpe, Beall, Fagan, Minnich & Mckee, LLP

[57] ABSTRACT

A disinfectant hand wash includes triclosan and a reduced amount of surfactants in order to reduce skin irritation while maintaining improved activity against Gram negative and Gram positive organisms, including *Serratia marcescens*. The hand wash includes an effective amount of triclosan, preferably 0.2–3.0% and a non-aqueous solvent. A mixture of hexylene glycol and isopropanol provide improved efficacy in killing skin-born microbes. The hand wash further includes 2–20% surfactant, preferably at less than 10%. The hand wash further includes a chelating agent, a thickener, a buffering agent, and water.

14 Claims, No Drawings

TRICLOSAN SKIN WASH WITH ENHANCED EFFICACY

This application claims the benefit of U.S. Provisional Application No. 60/021,453, filed Jul. 10, 1996.

BACKGROUND OF THE INVENTION

The present invention relates to the antimicrobial arts. It finds particular application in conjunction with the removal of microorganisms from the skin of health care personnel and will be described with particular reference thereto. It should be appreciated, however, that the invention is also applicable outside the medical area, such as a hand wash for workers in the food preparation industry, a wash for consumer and home health care, or other areas where skin disinfection is advisable.

The chemical control of bacteria and viruses is assuming increasing importance in the hospital and medical environment. The situation has been exacerbated by the failure of many bacteria to respond to conventional antibiotics. Accordingly, the need for effective control of bacterial and viral organisms is assuming greatly increased significance. In the case of hand and skin disinfection, a biocidal agent needs to kill the widest possible range of microorganisms in the least possible time without toxicity, irritation or other hazards.

SUMMARY OF THE INVENTION

In accordance with the present invention, an improved health care personnel skin wash is provided including:

(a) about 0.2 to about 3.0% triclosan;

(b) about 1.0 to about 30.0% non-aqueous solvent;

(c) about 2.0 to about 20.0% surfactant;

(d) 0.0 to about 1.0% chelating agent;

(e) 0.0 to about 3.0% thickener;

(f) 0.0 to about 5.0% buffering agent; and (g) the remainder water.

One advantage of the invention resides in improved activity against Gram negative organisms. In particular, the formulations have improved activity over other formulations against *Serratia marcescens,* a Gram negative organism which is one of the most difficult to kill.

Another advantage of the invention resides in improved activity against Gram positive organisms.

Other advantages of the invention include efficacy at low surfactant concentrations, a reduction in the skin irritation typically associated with triclosan hand wash formulations, and a superior cleaning effect to hand washes comprised primarily of alcohols.

Still further advantages of the present invention will become apparent to those of ordinary skill in the art upon reading and understanding the following detailed description of the preferred embodiments.

DETAILED DESCRIPTION OF THE PREFERRED EMBODIMENTS

Triclosan (5-chloro-2-(2,4-dichlorophenoxy)phenol) is present in the hand and skin wash formulations in an amount from about 0.2 to about 3.0%. Preferably, the amount of triclosan is from about 0.3 to about 1.5%.

Unfortunately, triclosan has very poor solubility in water and generally requires formulation additives to solubilize it. The most common additives used to solubilize triclosan are surfactants which increase skin irritation. The present formulations minimize this problem by using non-aqueous solvents and lower levels of surfactants to solubilize the triclosan.

The non-aqueous solvents used in the formulations are generally present in an amount from about 1.0 to about 30%. Preferably, these solvents are present in an amount from about 5.0 to about 25.0%. Examples of suitable non-aqueous solvents include glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations of these. Especially preferred are the combinations of hexylene glycol and isopropanol and hexylene glycol and n-propanol.

In prior art compositions, surfactants used to solubilize the triclosan are generally present in amounts of perhaps about 5–30% active surfactant by weight. The surfactants used in the present formulations are generally present in much lower amounts, for instance from about 2.0 to about 20.0%, and preferably in an amount from about 2.4 to about 10%.

Typical examples of surfactants which are useful in the formulations of the invention include nonionic and anionic surfactants such as polyoxyethylene sorbitan fatty acid esters, polyoxyethylene stearates, polyvinyl alcohol, poloxamers, octoxynols, sodium or ammonium salts of sarcosinates, sulfosuccinates, sulfonates, isethionates, sulfates, amine oxides, taurates, betaines, sultaines, imidazolines and their derivatives, and combinations of these. A preferred surfactant is ammonium cocoyl isethionate.

Chelating agents are used in an amount from 0.0 to about 1.0%. It is particularly preferred that the amount be from about 0.01 to about 0.5%. Typical examples of the kind of chelating agents which are useful in the present formulation include EDTA acid or salts, citric acid or salts, glucuronic acid or salts, pyrophosphate salts, chelating surfactants such as phosphate esters and lauroyl ethylenediaminetriacetic acid, and mixtures of these. The chelating agents serve to improve the effectiveness of the formulation toward Gram negative bacteria.

The polymer/viscosity-inducing agent, or thickener, is present in an amount from 0.0 to about 3.0%, and preferably in an amount from about 0.5 to about 2.0%. Typical examples of these agents include hydroxypropyl methylcellulose, hydroxypropyl cellulose, hydroxyethyl cellulose, carbomer, naturally occurring gums, such as guar, guar derivatives, alginate, and alginate derivatives, and mixtures of these.

The buffering agents are present in an amount from 0.0 to about 5.0%, and preferably in an amount from about 0.1 to about 1.0%. These agents are typically acids or salts used to maintain pH in the range of about 3.0 to about 8.0, and preferably from about 4.5 to about 6.0. Examples include acetic acid/acetate salts, citric acid/citrate salts, glycolic acid/glycolate salts, phosphoric acid/phosphate salts, and mixtures of any of these. The most preferred formulations include citric acid/citrate salts.

Finally, water is used to make up the remainder of the composition.

To prepare the hand wash, the components are mixed together in the proportions described. In order to solubilize the triclosan completely, it is preferably first mixed in the solvent(s) and/or surfactant(s) before the water is added. The other components are then added when convenient. When the components are mixed together in the proportions described, the viscosity of the composition formed is from about 20 to 10,000 cps. Preferably, the viscosity of the composition formed is from about 500 to 2500 cps.

As noted above, the present formulations have improved activity against Gram negative and Gram positive organisms. The activity against Gram negative organisms is most dramatic with the inclusion of low levels of isopropanol or n-propanol. Such activity is completely unexpected since low levels of isopropanol alone do not show this level of activity. The activity against Gram positive organisms is particularly evident when hexylene glycol is used as a solvent. Accordingly, combinations of isopropanol and hexylene glycol or n-propanol and hexylene glycol are preferred.

Additionally, as noted above, triclosan is poorly soluble in water and generally formulation additives are used to solubilize it. The most common additives used to solubilize triclosan are surfactants which often increase the irritancy of a formulation. The present formulations contain non-aqueous solvents and lower levels of surfactants to solubilize the triclosan. Propylene glycol is the most common choice of solvent for topical products. In the present formulations, hexylene glycol serves as a better solvent than propylene glycol. Accordingly, the preferred formulations include hexylene glycol and isopropanol.

The present formulations are applied to the skin surface to be treated in a conventional manner, as one would apply any hand wash or soap. Preferably, the hand wash is dispensed from a bottle or other dispenser and worked into the hands for sufficient time to remove soil and kill microorganisms present on the skin. Water is used to assist in the formation of a lather. To remove the hand wash, it is rinsed off with water.

EXAMPLES

Example 1

Samples of a triclosan formulation were inoculated with strains of microorganisms expected to be found on skin surfaces as transients or residents and the effectiveness of the formulation determined in terms of the log reduction in the number of microorganisms.

The following triclosan hand wash formulation was prepared:

| Material | % by Weight |
| --- | --- |
| Ammonium Hydroxide | 0.0870 |
| Triclosan | 1.0000 |
| Hexylene Glycol | 10.000 |
| Deionized Water | 69.8130 |
| Hydroxypropyl Methylcellulose | 0.9500 |
| (Brand - Methocel K15MS) | |
| Ammonium Cocoyl Isethionate | 15.0000 |
| (Brand - Jordapon ACI-30) | |
| Diammonium Dimethicone Copolyol | 1.5000 |
| Sulfosuccinate | |
| (Brand - Mackanate DC-60A) | |
| Ammonium Lauroyl Sarcosinate | 1.5000 |
| (Brand - Hamposyl AL-30) | |
| EDTA Acid | 0.1500 |
| (Brand - Hampene Acid) | |

As the ammonium cocoyl isethionate and the ammonium lauroyl sarcosinate were 30% solutions and the diammonium dimethicone copolyol sulfosuccinate a 60% solution, the total surfactant concentration in the hand wash formulation was 5.85% by weight.

Preparation of Inoculum

The organisms tested were chosen to represent a broad spectrum of standards and clinical isolates. Table 1 lists the organisms tested and their sources.

For Candida strains, 48 hours prior to testing, Yeast Maltose (YM) agar slants were inoculated with 0.1 mL of stock culture and incubated for 48 hours at 30° C. For other strains that were tested, 24 hours prior to testing, Brain Heart Infusion (BHI) agar slants were inoculated with 0.1 mL of stock culture and incubated at 30° C. for 24 hours. After incubation, the day of testing, cultures were removed from the incubator. Cultures were then resuspended with 10 mL of sterile 0.85% saline solution, yielding a suspension containing approximately $10^9$ organisms.

Time Kill Procedure 10 mL samples of the triclosan formula were inoculated with 0.1 mL of the approximate $10^9$ microorganism suspension and mixed.

At scheduled intervals, a 1.0 mL portion of the inoculated samples was removed and placed into a neutralizing dilution blank. The neutralizers used were Letheen broth containing 5% heat-inactivated fetal bovine serum for triclosan. Serial dilutions were performed and plated to the fifth dilution. Counts were compared with an inoculated control to quantify the log reduction of organisms due to the activity of the formulation. Log reduction is the difference between the log of the original number of organisms present and the log of the number remaining, thus an increase in log reduction over time indicates that an increasing number of organisms are destroyed.

The results are shown in Table 1. The data demonstrate that the triclosan-containing formulation exhibits activity against a broad spectrum of organisms. A range of activity is observed with the greatest rate and extent of kill seen for Gram positive organisms known to reside on skin and to be transferred via hands in the hospital setting.

TABLE 1

TIME KILL RESULTS FOR 1% TRICLOSAN HAND WASH FORMULATION

Sources of Strains
ATCC - American Type Culture Collection
SLU - St. Louis University Hospital, St. Louis, MO.
CH - Children's Hospital, St.Louis, MO.

| Organism | Isolate | Log Reduction Time (min) | | | |
| --- | --- | --- | --- | --- | --- |
| | | 0.25 | 0.50 | 1.00 | 2.00 |
| Gram Positive Organisms | ATCC 6538 | 7.76 | 7.76 | 7.76 | 7.76 |
| Staphylococcus aureus | ATCC 33591 | 0.38 | 0.48 | 0.47 | 0.86 |
| | ATCC 33591(2) | 0.40 | 0.60 | 0.67 | 1.15 |
| | ATCC 33592 | 7.69 | 7.69 | 7.69 | 7.69 |
| | ATCC 33593 | 7.91 | 7.91 | 7.91 | 7.91 |
| Methicillin-Resistant | SLU 253 | 3.73 | 7.68 | 7.68 | 7.68 |
| Staphylococcus aureus | CH 6 | 7.77 | 7.77 | 7.77 | 7.77 |
| | CH 12 | 3.42 | 7.95 | 7.95 | 7.95 |
| | CH 14 | 2.44 | 3.17 | 7.61 | 7.61 |
| | CH 23 | 7.60 | 7.60 | 7.60 | 7.60 |
| Staphylococcus epidermidis | ATCC 12228 | 1.22 | 2.82 | 7.42 | 7.42 |
| | ATCC 35983 | 0.52 | 0.85 | 2.46 | 3.90 |
| Staphylococcus epidermidis | CH 600 | 1.74 | 3.28 | 4.37 | 7.13 |
| | CH 601 | 2.17 | 6.07 | 6.07 | 6.07 |
| Streptococcus pyogenes | ATCC 8058 | 6.83 | 6.83 | 6.83 | 6.83 |
| | ATCC 19615 | 6.43 | 6.43 | 6.43 | 6.43 |
| | ATCC 21059 | 6.27 | 6.27 | 6.27 | 6.27 |
| | CH 39 | 6.58 | 6.58 | 6.58 | 6.58 |
| | BMS BMY 597 | 6.59 | 6.59 | 6.59 | 6.59 |
| | BMS BMY 600 | 6.49 | 6.49 | 6.49 | 6.49 |

TABLE 1-continued

TIME KILL RESULTS FOR 1% TRICLOSAN HAND WASH FORMULATION

Sources of Strains
ATCC - American Type Culture Collection
SLU - St. Louis University Hospital, St. Louis, MO.
CH - Children's Hospital, St.Louis, MO.

| Organism | Isolate | Log Reduction Time (min) | | | |
|---|---|---|---|---|---|
| | | 0.25 | 0.50 | 1.00 | 2.00 |
| *Enterococcus faecalis* | ATCC 27959 | 6.64 | 6.64 | 6.64 | 6.64 |
| | ATCC 29212 | 6.93 | 6.93 | 6.93 | 6.93 |
| | ATCC 29302 | 7.01 | 7.01 | 7.01 | 7.01 |
| | ATCC 33186 | 7.17 | 7.17 | 7.17 | 7.17 |
| Vancomycin-Resistant | A | 1.19 | 2.47 | 1.24 | 6.35 |
| *Enterococcus faecium* | E | 1.51 | 2.58 | 3.51 | 4.68 |
| | G | 3.85 | 6.67 | 6.67 | 6.67 |
| | G(2) | 2.57 | 3.44 | 4.38 | 6.49 |
| | H | 4.24 | 6.29 | 6.29 | 6.29 |
| Gram Negative | ATCC 26 | 0.31 | 0.76 | 1.32 | 2.93 |
| Organisms | ATCC 8739 | 0.35 | 0.37 | 0.86 | 2.53 |
| *Escherichia coli* | ATCC 11229 | −0.57 | −0.43 | 0.54 | 0.27 |
| | ATCC 15221 | 0.04 | 0.14 | 1.19 | 4.21 |
| *Escherichia coli* | CH 400 | 0.10 | 0.27 | 0.70 | 2.96 |
| | CH 401 | 0.38 | 0.36 | 0.75 | 2.54 |
| | CH 402 | 0.26 | 0.07 | 0.30 | 0.79 |
| *Klebsiella pneumoniae* | ATCC 8044 | 0.38 | 0.72 | 1.49 | 2.68 |
| | ATCC 13883 | 0.45 | 0.40 | 1.07 | 1.41 |
| | ATCC 27736 | 0.05 | 0.01 | 0.24 | 0.43 |
| | ATCC 33452 | 0.49 | 0.60 | 1.06 | 1.08 |
| | CH 500 | 0.05 | 0.19 | 0.15 | 0.47 |
| | CH 501 | −0.15 | −0.12 | −0.04 | 0.10 |
| | CH 502 | 0.26 | 0.15 | 0.22 | 0.30 |
| *Pseudomonas aeruginosa* | ATCC 9027 | 7.32 | 7.32 | 7.32 | 7.32 |
| | ATCC 14502 | 2.88 | 3.88 | 7.36 | 7.36 |
| | ATCC 15442 | 4.98 | 8.02 | 8.02 | 8.02 |
| | ATCC 27853 | 6.29 | 4.41 | 7.76 | 7.76 |
| | CH 300 | 5.58 | 8.11 | 8.11 | 8.11 |
| | CH 301 | 4.69 | 7.94 | 7.94 | 7.94 |
| | CH 302 | 7.79 | 7.79 | 7.79 | 7.79 |
| | CH 303 | 3.47 | 7.93 | 7.93 | 7.93 |
| *Serratia marcascens* | ATCC 8195 | 0.56 | 0.60 | 0.79 | 0.96 |
| | ATCC 14756 | 0.18 | 0.29 | 0.37 | 0.41 |
| | CH 200 | 0.18 | 0.28 | 0.49 | 0.47 |
| | CH 201 | 0.22 | −0.08 | 0.25 | 0.65 |
| Yeast | ATCC 10259 | 0.37 | 0.27 | 0.62 | 0.81 |
| *Candida albicans* | ATCC 18804 | −0.61 | −0.65 | −0.15 | −0.04 |
| | ATCC 24433 | −0.24 | 0.02 | 0.23 | 0.28 |
| | ATCC 38483 | 0.13 | 0.07 | 0.75 | 0.95 |
| | CH 100 | 0.32 | 0.03 | 0.11 | 0.23 |
| | CH 101 | 0.23 | −0.07 | 0.02 | 0.13 |
| | CH 102 | 0.30 | 0.10 | 0.24 | 0.46 |
| | CH 103 | 0.16 | 0.16 | 0.21 | 0.76 |

Example 2

The triclosan hand wash composition was modified according to the formula listed below and the procedures described in Example 1 repeated to determine the effectiveness of the modified formulation for destruction of the microorganisms listed in table 2. The neutralisers used in this example were Letheen broth containing either 5% heat-inactivated fetal bovine serum or 6% of a 3.5% asolecithin and 25% Tween 80 solution. The results shown in table 2 indicate that the modified formula was effective at destroying all organisms tested, even the Gram negative organisms such as *Serratia marcescens* that proved somewhat resistant to the formula used in Example 1. Of those organisms that were not completely destroyed within two minutes of exposure to the modified triclosan formulation, all were destroyed within a total of 3–5 minutes exposure.

| Modified Triclosan Hand Wash Formulation | |
|---|---|
| Ingredient | % by Weight |
| Triclosan | 1.0 |
| Ammonium Cocoyl Isethionate (30%) | 12.0 |
| Hexylene Glycol | 13.0 |
| Isopropyl alcohol | 5.0 |
| Hydroxypropyl methyl cellulose | 0.85 |
| Diammonium EDTA | 0.4 |
| Citric Acid | 0.05 q.s. to pH 5.0–5.5 |
| Deionized water | 67.72 |

TABLE 2

TIME KILL RESULTS FOR MODIFIED 1% TRICLOSAN HAND WASH FORMULATION

Sources of Strains
ATCC - American Type Culture Collection
SLU - St. Louis University Hospital, St. Louis, MO.
CH - Children's Hospital, St. Louis, MO.
Baseline counts are indicated under "isolate".

| Organism | Isolate | Log Reduction Time (min) | | | |
|---|---|---|---|---|---|
| | | 0.25 | 0.50 | 1.00 | 2.00 |
| Gram Positive Organisms | ATCC 6538 (7.8) | 7.80 | 7.80 | 7.78 | 7.80 |
| *Stsphylococcus aureus* | ATCC 33591 (7.25) | 7.25 | 7.25 | 7.25 | 7.25 |
| | ATCC 33592 (7.0) | 7.00 | 7.00 | 7.00 | 7.00 |
| | ATCC 33593 (7.68 | 7.91 | 7.91 | 7.91 | 7.91 |
| Methicillin-Resistant | SLU 253 (6.98) | 6.98 | 6.98 | 76.98 | 6.98 |
| *Staphylococcus aureus* | CH 6 (7.64) | 7.64 | 7.64 | 7.64 | 7.64 |
| | CH 12 (7.95) | 7.95 | 7.95 | 7.95 | 7.95 |
| | CH 14 (7.49) | 7.49 | 7.49 | 7.49 | 7.49 |
| *Staphylococcus epidermidis* | ATCC 12228 (6.66) | 6.66 | 6.66 | 6.66 | 6.66 |
| | ATCC 35983 (7.16) | 7.16 | 7.16 | 7.16 | 7.16 |
| *Staphylococcus epidermidis* | CH 600 (7.13) | 7.13 | 7.13 | 7.13 | 7.13 |
| | CH 601 (7.69) | 7.69 | 7.69 | 7.69 | 7.69 |
| *Enterococcus faecalis* | ATCC 27959 (7.08) | 7.08 | 7.08 | 7.08 | 7.08 |
| | ATCC 29212 (7.42) | 7.42 | 7.42 | 7.42 | 7.42 |
| | ATCC 29302 (7.58) | 7.58 | 7.58 | 7.58 | 7.58 |
| | ATCC 33186 (7.55) | 7.55 | 7.55 | 7.55 | 7.55 |
| Vancomycin-Resistant | A (6.64) | 4.80 | 6.64 | 6.64 | 6.64 |
| *Enterococcus faecium* | E (6.60) | 6.60 | 6.60 | 6.60 | 6.60 |
| | G (6.58) | 6.58 | 6.58 | 6.58 | 6.58 |
| | H (6.69) | 6.69 | 6.69 | 6.69 | 6.69 |
| Gram Negative Organisms | ATCC 26 (7.71) | 0.92 | 2.02 | 5.40 | 7.71 |
| | ATCC 8739 (7.98) | 1.17 | 3.14 | 7.98 | 7.98 |
| *Escherichia coli* | ATCC 11229 (7.61) | 0.66 | 1.88 | 6.13 | 7.61 |
| | ATCC 15221 (7.74) | 0.83 | 0.93 | 2.77 | 7.74 |
| *Escherichia coli* | CH 400 (7.78) | 0.42 | 1.07 | 3.93 | 7.78 |
| | CH 401 (7.75) | 0.67 | 1.27 | 3.29 | 7.75 |
| | CH 402 (7.84) | 0.75 | 0.82 | 1.57 | 4.94 |
| *Pseudomonas aeruginosa* | ATCC 9027 (7.67) | 7.67 | 7.67 | 7.67 | 7.67 |
| | ATCC 14502 (7.49) | 7.49 | 7.49 | 7.49 | 7.49 |
| | ATCC 15442 (7.92) | 7.92 | 7.92 | 7.92 | 7.92 |
| | ATCC 27853 | 7.70 | 7.70 | 7.70 | 7.70 |

TABLE 2-continued

TIME KILL RESULTS FOR MODIFIED 1% TRICLOSAN HAND WASH FORMULATION

Sources of Strains
ATCC - American Type Culture Collection
SLU - St. Louis University Hospital, St. Louis, MO.
CH - Children's Hospital, St. Louis, MO.
Baseline counts are indicated under "isolate".

| Organism | Isolate | Log Reduction Time (min) | | | |
|---|---|---|---|---|---|
| | | 0.25 | 0.50 | 1.00 | 2.00 |
| | (7.7) | | | | |
| | CH 300 (7.89) | 7.89 | 7.89 | 7.89 | 7.89 |
| | CH 301 (7.77) | 7.77 | 7.77 | 7.77 | 7.77 |
| | CH 302 (7.62) | 7.62 | 7.62 | 7.62 | 7.62 |
| | CH 303 (7.42) | 7.42 | 7.42 | 7.42 | 7.42 |
| Serratia marcescens | ATCC 8195 (7.68) | 0.27 | 1.76 | 4.39 | 7.68 |
| | ATCC 14756 (8.01) | 0.21 | 0.44 | 1.30 | 3.45 |
| | CH 200 (7.67) | 0.07 | 0.22 | 0.98 | 1.57 |
| | CH 201 (7.80) | 0.42 | 0.56 | 1.65 | 5.76 |

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A skin wash composition comprising:
    (a) about 0.2 to about 3.0% Triclosan;
    (b) about 1.0 to about 30.0% non-aqueous solvent which includes hexylene glycol;
    (c) less than 10.0% total surfactant, including at least 2.4% alkyl isethionate;
    (d) about 0.0 to about 1.0% chelating agent;
    (e) about 0.0 to about 3.0% thickener;
    (f) about 0.0 to about 5.0% buffering agent; and
    (g) water.

2. The skin wash of claim 1, wherein the Triclosan is at a concentration of 0.3 to 1.5%.

3. The skin wash of claim 1, wherein the non-aqueous solvent further includes one or more of the group including glycols, alcohols, triglycerides, ethyl acetate, acetone, and triacetin.

4. The skin wash of claim 3, wherein the non-aqueous solvent further includes one or more of the group including propylene glycol, butylene glycol, triethylene glycol, polyethylene glycol, ethoxydiglycol, dipropyleneglycol, ethanol, n-propanol, isopropanol, triglycerides, ethyl acetate, acetone, and triacetin.

5. The skin wash of claim 4, wherein the non-aqueous solvent includes between about 5 and 13% hexylene glycol and about 5% isopropanol, n-propanol, or mixtures thereof.

6. The skin wash of claim 1, wherein the surfactant further includes one or more of the group including polyoxyethylene sorbitan fatty acid esters, polyoxyethylene stearates, polyvinyl alcohol, poloxamers, octoxynols, sodium or ammonium salts of sarcosinates, sulfonates, sulfosuccinates, sulfates, amine oxides, taurates, betaines, sultaines, imidazolines, and their derivatives.

7. The skin wash of claim 1, wherein the alkyl isethionate includes ammonium cocoyl isethionate.

8. The skin wash of claim 1, wherein the chelating agent includes one or more of the group including EDTA acid or salts, citric acid or salts, glucuronic acid or salts, pyrophosphate salts, and chelating surfactants.

9. The skin wash of claim 1, wherein the thickener includes one or more of the group including hydroxypropyl methylcellulose, hydroxypropyl cellulose, hydroxyethyl cellulose, guar and guar derivatives, alginate and alginate derivatives, and carbomer.

10. The skin wash of claim 1, wherein the buffering agent includes one or more of the group including acetic acid or acetate salts, citric acid or citrate salts, glycolic acid or glycolate salts, and phosphoric acid or phosphate salts.

11. The skin wash of claim 10, wherein the buffering agent includes citric acid or citrate salts.

12. The skin wash of claim 7, wherein the surfactant is at a concentration of about 5.85% or below.

13. A method of disinfecting skin comprising:
    a) applying to the skin a cleaning effective amount of a composition including:
        about 0.2 to about 3.0% Triclosan;
        about 1.0 to about 30.0% of a non-aqueous solvent which includes hexylene glycol;
        about 2.0 to about 10% surfactant including at least 2.4% alkyl isethionate;
        about 0.1 to about 1.0% chelating agent;
        about 0.0 to about 3.0% thickener;
        about 0.1 to about 5.0% buffering agent; and water; and,
    b) maintaining contact between the composition and the skin for sufficient time to kill substantially all microorganisms present on the surface.

14. The method of claim 13, further including adding water and rubbing the surface, thereby removing soil from the surface, followed by rinsing the composition from the skin.

* * * * *